(12) United States Patent
Tsui

(10) Patent No.: US 6,190,370 B1
(45) Date of Patent: Feb. 20, 2001

(54) DEVICES, SYSTEMS AND METHODS FOR DETERMINING PROPER PLACEMENT OF EPIDURAL CATHETERS

(75) Inventor: Ban C. H. Tsui, Edmonton (CA)

(73) Assignee: Arrow International, Inc., Reading, PA (US)

(*) Notice: Under 35 U.S.C. 154(b), the term of this patent shall be extended for 0 days.

(21) Appl. No.: 09/269,155

(22) PCT Filed: Jul. 24, 1998

(86) PCT No.: PCT/CA98/00720
§ 371 Date: Feb. 26, 1999
§ 102(e) Date: Feb. 26, 1999

(87) PCT Pub. No.: WO99/04705
PCT Pub. Date: Feb. 4, 1999

Related U.S. Application Data
(60) Provisional application No. 60/053,716, filed on Jul. 25, 1997.

(51) Int. Cl.[7] .................................................. A61M 31/00
(52) U.S. Cl. ............................................ 604/508; 604/117
(58) Field of Search ........................ 604/117, 20, 164.01, 604/164.09, 158, 162, 503, 505, 508, 512, 22, 164.11; 607/117, 101; 128/898; 606/41, 42

(56) References Cited

U.S. PATENT DOCUMENTS

| | | |
|---|---|---|
| 3,682,162 | 8/1972 | Colyer . |
| 4,518,383 | 5/1985 | Evans . |
| 4,644,960 | 2/1987 | Johans . |
| 4,737,146 | 4/1988 | Amaki et al. . |
| 4,919,653 * | 4/1990 | Martinez et al. .................... 604/117 |
| 4,973,312 | 11/1990 | Andrew . |
| 4,985,022 | 1/1991 | Fearnot et al. . |
| 5,007,902 | 4/1991 | Witt . |
| 5,024,662 | 6/1991 | Menes et al. . |

(List continued on next page.)

FOREIGN PATENT DOCUMENTS

| | | |
|---|---|---|
| 6 88 03 153 | 6/1988 | (DE) . |
| 2026069 | 9/1970 | (FR) . |
| 9314710 | 8/1993 | (WO) . |
| 9320751 | 10/1993 | (WO) . |

OTHER PUBLICATIONS

Chen, C.F. et. al., "A New Recognizing Method of Epidural Space for Epidural Anesthesia," Proceedings of the Ninth Annual Conference of the IEEE Engineering in Medicine and Biology Society, Boston, Nov. 13–16, 1987, vol. 2, pp. 429–430.

Contiplex Insulated Tuohy Needle—Continuous Peripheral Nerve Blockade System for a Wide Range of Orthopedic Procedures, Braun & McGaw materials, undated (2 pages).

Englesson, Soren, "Lumbar Epidural Anaesthesia," *Illustrated Handbook in Local Anaesthesia*, Eriksson Ejnar, Editor, pp. 121–128.

Primary Examiner—Anhtuan T. Nguyen
(74) Attorney, Agent, or Firm—Amster, Rothstein & Ebenstein

(57) ABSTRACT

Methods and systems for determining the proper placement of an epidural catheter prior to administration of anesthetic is described. In a preferred embodiment, an aqueous fluid is introduced into an epidural catheter that has been inserted into the spine of a subject. Motor reactions by the subject in response to electrical current applied through the aqueous solution is monitored. By monitoring the motor response with respect to electrical stimulation, the proper placement of an epidural catheter can be differentiated from the placement of the catheter in subarachnoid, subcutaneous or epidural intravascular placement. Additionally, in the preferred embodiment, a wire is disposed within the catheter tube to facilitate the passage of electric current. However, to avoid electrochemical reaction of the wire with the aqueous solution and/or the subject's dural tissue, the wire does not extend completely to the distal end of the catheter tube.

32 Claims, 6 Drawing Sheets

U.S. PATENT DOCUMENTS

| | | |
|---|---|---|
| 5,069,674 | 12/1991 | Fearnot et al. . |
| 5,081,990 | 1/1992 | Deletis . |
| 5,135,525 | 8/1992 | Biscoping et al. . |
| 5,423,877 | 6/1995 | Mackey . |
| 5,464,400 | 11/1995 | Collins . |
| 5,545,648 | 8/1996 | Hansebout et al. . |
| 5,628,734 | 5/1997 | Hatfalvi . |

\* cited by examiner

DEVICES, SYSTEMS AND METHODS FOR DETERMINING PROPER PLACEMENT OF EPIDURAL CATHETERS

This application claims benefit to Provisional application 60/053,716 filed Jul. 25, 1997.

FIELD OF THE INVENTION

This invention relates to the field of catheters and, more particularly, relates to a method and to a system for inserting catheters for administering epidtal anesthesia and for confirming the placement of a catheter in an epidural space of a spine of a subject.

BACKGROUND

Catheters of various types and sizes have been used by physicians extensively. One use of the catheter is in providing regional anesthesia with minimal physiologic alterations. When used at the start of an operation, regional anesthesia minimizes the total dosage of inhalation or intravenous anesthetic drugs required, hastens awakening, and permits early ambulation. When administered at the conclusion of surgery, regional anesthesia produces post-operative analgesia with reduced risk of respiratory depression.

When prolonged analgesia is required, a catheter is inserted into the caudal or lumbar epidural space to provide intermittent or continuous injections of local anesthetics. Continuous lumbar epidural anesthesia is a well-established and accepted technique in adult patients. It differs from caudal epidural anesthesia by the location where the needle is inserted. Caudal epidural anesthesia, however, is notable for its simplicity, safety, and effectiveness and is one of the most frequently used regional anesthetic techniques for operations below the diaphragm in children.

Epidural and spinal anesthesia require the administration of an anesthetic agent into the epidural or subaractmoid spaces respectively of the spine. Epidural anesthesia requires substantially more anesthetic agent than spinal anesthesia and, if the anesthetist inadvertently penetrates the duraarachnoid membrane while endeavoring to administer an anesthetic agent to the epidural space, a dangerous quantity of anesthetic agent can be placed in the subaradmoid space, possibly causing paralysis or even death.

The majority of physicians prefer the use of the midline approach for spinal puncture. Generally, with the midline approach, the spinal injection is made at the center of the patient's back with the needle oriented in a plane parallel to the centerline of the spine. The needle tip is inserted into the back in a straight line toward the midline of the spine (2) between the second (4) and third (6) lumbar vertebrae, a direction generally represented by the arrow (A) shown in FIG. 1. In this technique the epidural needle passes through the supraspinous, inrterspyious and ligamentum flavum structures before entering the epidural space, hisertion of the needle into the epidural space is complicated by the lack of feedback as to the position of the needle tip, coupled with the imperative need to avoid puncturing the dura mater which surrounds the spinal cord, since there is potential for catastrophic trauma to the spinal cord with the epidural needle. Extreme caution must therefore be exercised in the positioning of the needle tip, which must pierce through the tough, resilient, leather-like ligamentum flavum, and then stop immediately within the narrow epidural space, short of puncturing the dura mater.

The needle must be moved through the ligamentum flavum very slowly and in a carefully controlled fashion. At the same time, pressure is applied to the plunger of the attached syringe which is filled either with air or saline solution. The object is to continuously test for loss of resistance to injection, experienced when the needle lumen enters the epidural space after clearing the ligamentum flavum. This loss of resistance is experienced by little if any resistance to injected air or fluid, and a negative aspiration test then indicates that the needle lumen is properly positioned in the epidural space. Special syringes, known as loss of resistance syringes and characterized by very low friction between the plunger and the barrel of the syringe, are used for positioning the needle lumen in the epidural space. Once correct positioning of the needle is achieved, the resistance syringe is separated from the epidural needle and another syringe, loaded with the anesthetic is attached, after which the anesthetic is injected.

It is important to understand the demands placed upon the anesthesiologist's dexterity by this procedure. It is of critical importance that the needle traverse t ligamentum flavum in a carefully measured and controlled manner. Typically, this is achieved by applying resistance to the advancing needle with the anesthesiologist's non-dominant hand (the left-hand if the anesthesiologist is right-handed) while the dominant hand applies pressure to the plunger of the resistance syringe to test for resistance to injection while at the same time slowly advances the needle. Variations of this technique may be adopted according to personal preference, for example the needle may be advanced continuously while pressure on the syringe barrel is also maintained continuously to test for resistance. In the alternative, the needle is advanced in very small increments, e.g., 1 millimeter, testing for resistance to injection after each advance.

The difficulty of correctly positioning the needle lumen in the epidural space has spurred many attempts to develop methods and devices for detecting and indicating correct needle placement. These approaches have generally exploited the low resistance to injection and subatmospheric pressure characteristic of the epidural space. One such technique involves placement of a drop of saline solution on the open hub of an epidural needle. The drop will be "sucked-in" as the needle lumen enters the epidural space where, for reasons not well understood, prevails subatmospheric pressure. Other means used for this purpose include capillary attachments with fluid indicators developed by Odom, or inflated balloons by Macintosh, which deflate upon entering the epidural space. It is also known to use spring loading devices to facilitate the loss of resistance phenomena which occur as the epidural needle passes from the dense ligamentum flavum into the lesser resistance of the epidural space.

U.S. Pat. No. 5,024,662, describes an attachment for a resistance syringe for aiding the anesthesiologist in correct placement of the epidural needle. The attachment has an elastomeric band retained to the syringe barrel by a ring which slides onto the syringe barrel against the finger flange of the syringe to anchor the ends of the elastic band to the barrel while a midportion of the band is pulled by the plunger of the syringe. Consequently, the plunger is urged by elastic force into the syringe barrel, but is held back by fluid, air or liquid in the barrel, until the needle lumen enters the epidural space. At that point the contents of the syringe are injected into the epidural space under the force of the stretched band, providing the anesthesiologist with immediate kinesthetic indication of correct needle placement. While this arrangement works well, disposable elastomeric drivers have been developed by this applicant which are of still greater simplicity and very low cost.

U.S. Pat. No. 4,518,383 teaches an instrument for epidural and spinal anesthesia in which an outer hollow Tuohy™ needle has a bent pointed tip to locate the epidural space and an inner hollow needle with a pointed tip projecting forwardly of the outer Tuohy™ needle in alignment therewith to penetrate the dura with a minimum of cutting of tissue. Likewise, U.S. Pat. No. 4,737,146 discloses another version of epidural catheter in which a rigid epidural needle is inserted into an epidural space and an epidural catheter is introduced through the needle into the epidural space through a lateral opening in the tip of the needle.

U.S. Pat. No. 5,081,990 describes catheters for epidural injection of drugs with electrodes at the distal end for measuring effect of the drugs. This device, however, is not used for determining the placement of the catheter prior to medicant injection and, by placing electrodes into the epidural space and directly contacting the dural tissue, risks electrochemical reaction between the electrode and the dural tissue in the presence of medicament, saline or body fluids.

U.S. Pat. No. 5,423,877 describes a catheter for simultaneous application of electrical stimulation and infusion of analgesic medication to nerve fibers in the spinal cord. The correct placement of the catheter requires constant communicating with the patient to determine the paresthesia in corresponding dermatome and myotome regions. Therefore, the determination of proper catheter location is only possible and limited to a certain group of patients with conscious, communicable, cooperative, calm and oriented state. In addition, such determination is depended on only subjective but not objective evaluation and the results tend to be unreliable and time consuming to obtain.

Additionally, as the metal electrodes are set distally at the end of the catheter tubing, correct placement of the electrode may be detected, but proper delivery of the injected anesthetic may not be reliably established. For instance, the injected anesthetic may leak proximal to the epidural space if there is any damage to the catheter during the insertion procedure.

Therefore, presently the confirmation of catheter placement can be made only after observing the clinical effects from subsequent local anesthesia drug injection. This clinical effect may take up to twenty minutes, depending on the type of local anesthesia injected. What is needed is a simple, rapid and effective method of determining proper placement of the catheter prior to the introduction of anesthesia.

SUMMARY OF THE INVENTION

The present invention provides systems and methods for determining the proper insertion and for confirming the proper placement of a spinal or epidural catheter. In one embodiment, a method comprises: a) providing: i) a subject in need of having a catheter inserted in the spine; ii) an epidural catheter having first and second ends; iii) an aqueous solution capable of conducting electricity and suitable for administration in the epidural space of said spine of said subject; and iv) an electrical conduction means; b) contacting the epidural space of the spine of said subject with said first end of said catheter; c) attaching said electrical conduction means to said second end of said catheter; d) administering said aqueous solution through said catheter into said epidural space; and e) conducting electricity with said electrical conduction means under conditions such that said aqueous solution conducts electricity in said epidural space. In a preferred embodiment, the methods further comprise the step f) measuring the motor response of said subject caused by said conducting of electricity. While the present invention is not limited by the type of electrical conduction means, in one embodiment, the electrical conduction means comprises a connector configured for attachment to said second end of said catheter and having a conductive element in communication with a source of electricity.

In another embodiment, the methods comprise: a) providing: i) a subject in need of having a catheter inserted in the spine; ii) a non-metal-containing epidural catheter having first and second ends; iii) an aqueous solution capable of conducting electricity and suitable for administration in the epidural space of said spine of said subject; and iv) a connector configured for attachment to said second end of said catheter, said connector having a conductive element in communication with a source of electricity; b) contacting the epidural space of said spine of said subject with said first end of said catheter; c) attaching said connector to said second end of said catheter; d) administering said aqueous solution through said catheter into said epidural space; e) conducting electricity with said conductive element of said connector under conditions such that said aqueous solution conducts electricity in said epidural space; and f) measuring the motor response of said subject caused by said conducting of electricity. In a preferred embodiment, the methods further comprise the step g) administering an anesthetic to said subject.

In another embodiment, the methods comprise: a) providing: i) a subject in need of having a catheter inserted into the spine; ii) an epidural catheter having first and second ends, said catheter comprising a metal element disposed within the length of the catheter and housed completely within said catheter such that no Metal is exposed outside said first end of said catheter; iii) an aqueous solution capable of conducting electricity and suitable for administration in the epidural space of said spine of said subject; and iv) a connector configured for attachment to said second end of said catheter, said connector having a conductive element in communication with said metal element and a source of electricity; b) contacting the epidural space of said spine of said subject with said first end of said catheter; c) attaching said connector to said second end of said catheter; d) administering said aqueous solution through said catheter into said epidural space; e) conducting electricity with said conductive element of said connector under conditions such that said aqueous solution conducts electricity in said epidural space; and f) measuring the motor response of said subject caused by said conducting of electricity. In a preferred embodiment, the methods further comprise the step g) administering an anesthetic to said subject. The present invention is not limited by the nature of the metal element. In one embodiment, the metal element comprises a wire disposed within said catheter; in a preferred embodiment, said wire contacts said connector directly.

In another embodiment, a method is provided for confirming the placement of a catheter in an epidural space of a spine of a subject, the catheter having a proximal end and a distal end. The method comprises the steps of: (a) inserting the distal end of the catheter into the spine of the subject for contact with the epidural space; (b) conducting electricity to the distal end of the catheter, and (c) observing a motor response of the subject caused by conducting the electricity to the distal end of the catheter in order to confirm the placement of the catheter in the epidural space. The method may further comprise the step of adjusting the position of the catheter such that the distal end of the catheter contacts the epidural space of the spine of the sect. As well, this method may further comprise the step of administering an anesthetic to the subject.

In addition, the electricity may be conducted to the distal end of the catheter, at least in part, by electrical conduction means. The electrical conduction means may be comprised of a conductive element in communication with a source of electricity. Further, the conductive element may be comprised of a metal element disposed within the catheter. As indicated above, the metal element may be comprised of a wire. However, alternately, the metal element may be comprised of a removable needle having a distal end. The removable needle may be disposed within the catheter such that no portion of the needle is exposed outside the distal end of the catheter. However, when the metal element is comprised of a removable needle, the needle is preferably disposed within the catheter such that the distal end of the needle is exposed outside the distal end of the catheter for contacting the epidural space of the spine of the subject. Either a hollow or a non-hollow needle may be used. However, the needle is preferably hollow such that fluids may be conducted therethrough.

Preferably, the exposed distal end of the needle is not left in the epidural space for extended periods of time. Therefore, once the location or placement of the catheter is confirmed by electrical stimulation, the removable needle is preferably removed or withdrawn, at least in part, such that the distal end of the needle is no longer exposed outside the distal end of the catheter so that the metal of the needle is no longer in direct contact with the epidural space. More preferably, the needle is withdrawn completely from the catheter so that no rigid objects or elements remain in the epidural space of the subject.

Alternately, the catheter itself may be comprised of a hollow needle such that fluids may be conducted therethrough to a distal end of the needle. The fluids may be conducted directly through the bore of the needle or through a suitable second catheter, having an outside diameter smaller than the diameter of the bore of the needle, which may be inserted in the bore. The distal end of the needle defines the distal end of the catheter for contacting the epidural space of the spine of the subject. In this case, the conducting step of this embodiment of the method is comprised of conducting electricity to the distal end of the needle. Further, the needle may include an insulating coating about at least a portion of the needle, wherein the distal end of the needle is exposed outside the insulating coating Preferably, the hollow needle is not left in the epidural space for extended periods of time. Therefore, once the location or placement of the catheter is confirmed by electrical stimulation, an injection of an anesthetic or other medication may be introduced into the epidural space and the hollow needle is preferably subsequently withdrawn. Further, the second smaller diameter catheter described above may be inserted into the epidural space through the bore of the needle. The second smaller diameter catheter may be left in the epidural space and used for the administration of medications following the withdrawal or removal of the needle.

In another preferred embodiment, the methods further comprise the introduction of a test dose of anesthetic into the epidural space and monitoring of the minimum current required to induce a motor response in the subject. In this manner, it is possible to ascertain whether a catheter placed in an epidural space is improperly placed intravascularly. In one embodiment, the test dose is lidocaine, and in a preferred embodiment the test dose comprises 3 to 6 ml of 1.5% lidocaine.

The present invention is not limited by the condition of the subject, in one embodiment, the subject is unable to communicate; in such an embodiment, the subject may be unconscious. Likewise, the present invention is not limited by the nature of the aqueous solution. In one embodiment, the aqueous solution comprises a saline solution, while in another embodiment, the aqueous solution comprises epimorphine solution.

In one embodiment, the systems of the present invention comprise: a) an epidural catheter having first and second ends, said first end suitable for administration of fluids in the epidural space of the spine of a subject; and b) a connector attached to said second end of said catheter, said connector having a conductive element suitable for communication with a source of electricity. Another embodiment comprises a system, comprising. a) a metal-containing catheter having first and second ends, said first end suitable for administration of fluids in the epidural space of the spine of a subject, said catheter comprising a metal element disposed the length of said catheter and housed completely within said catheter such that no metal is exposed outside said first end of said catheter; and b) a connector attached to said second end of said catheter, said connector having a conductive element suitable for communication with a source of electricity.

In another embodiment, the present invention comprises a device, comprising a connector having first and second ends and a conductive element, said connector being dimensioned such that it is suitable for attachment to a catheter that is suitable for insertion into an epidural space of the spine of a subject. In a preferred embodiment, the device further comprises a catheter, having a distal end, suitable for insertion into an epidural space of the spine of a subject, wherein said first end of said connector is attached to said catheter. In a particularly preferred embodiment, the device further comprises a metal element disposed within said catheter. If desired, the metal element is disposed within the length of said catheter and housed completely within said catheter such that no metal is exposed outside said distal end of said catheter.

In still a further embodiment, the invention comprises a device for confirming the placement of a catheter in an epidural space of a spine of a subject. The device is comprised of the catheter having a distal end for contacting the epidural space of the spine of the subject and electrical conduction means in communication with the catheter for conducting electricity, at least in part, to the distal end of the catheter to cause a motor response of the subject in order to confirm the placement of the catheter in the epidural space.

In this embodiment, the electrical conduction means may be comprised of a conductive element in communication with a source of electricity. Further, the conductive element may be comprised of a metal element disposed within the catheter. The metal element may be comprised of a removable needle having a distal end. The removable needle may be disposed within the catheter such that no portion of the needle is exposed outside the distal end of the catheter. However, the removable needle is preferably disposed within the catheter such that the distal end of the needle is exposed outside the distal end of the catheter for contacting the epidural space of the spine of the subject. Either a hollow or a non-hollow needle may be used. However, the needle is preferably hollow such that fluids may be conducted therethrough.

Preferably, the exposed distal end of the needle is not left in the epidural space for extended periods of time. Therefore, once the location or placement of the catheter is confirmed by electrical stimulation, the removable needle is preferably removed or withdrawn, at least in part, such that the distal end of the needle is no longer exposed outside the distal end of the catheter so that the metal of the needle is no longer in direct contact with the epidural space. More preferably, the needle is withdrawn completely from the catheter so that no rigid objects or elements remain in the epidural space of the subject.

Alternately the device may be comprised of: (a) the catheter having a distal end for contacting the epidural space of the spine of a subject, wherein the catheter is comprised of a hollow needle such that fluids may be conducted therethrough to a distal end of the needle and wherein the distal end of the needle defines the distal end of the catheter for contacting the epidural space of the spine of the subject; and (b) a source of electricity in communication with the needle such that electricity is conducted to the distal end of the needle to cause a motor response of the subject in order to confirm the placement of the catheter in the epidural space. The fluids may be conducted directly through the bore of the needle or through a suitable second catheter, having an outside diameter smaller than the diameter of the bore of the needle, which may be inserted in the bore. Further, the needle may include an insulating coating about at least a portion of the needle, wherein the distal end of the needle is exposed outside the insulating coating.

Preferably, the hollow needle is not left in the epidural space for extended periods of time. Therefore, once the location or placement of the catheter is confirmed by electrical stimulation, an injection of an anesthetic or other medication may be introduced into the epidural space and the hollow needle is preferably subsequently withdrawn. Further, the second smaller diameter catheter described above may be inserted into the epidural space through the bore of the needle. The second smaller diameter catheter may be left in the epidural space and used for the administration of medications following the withdrawal or removal of the needle.

DEFINITIONS

Figure 1:
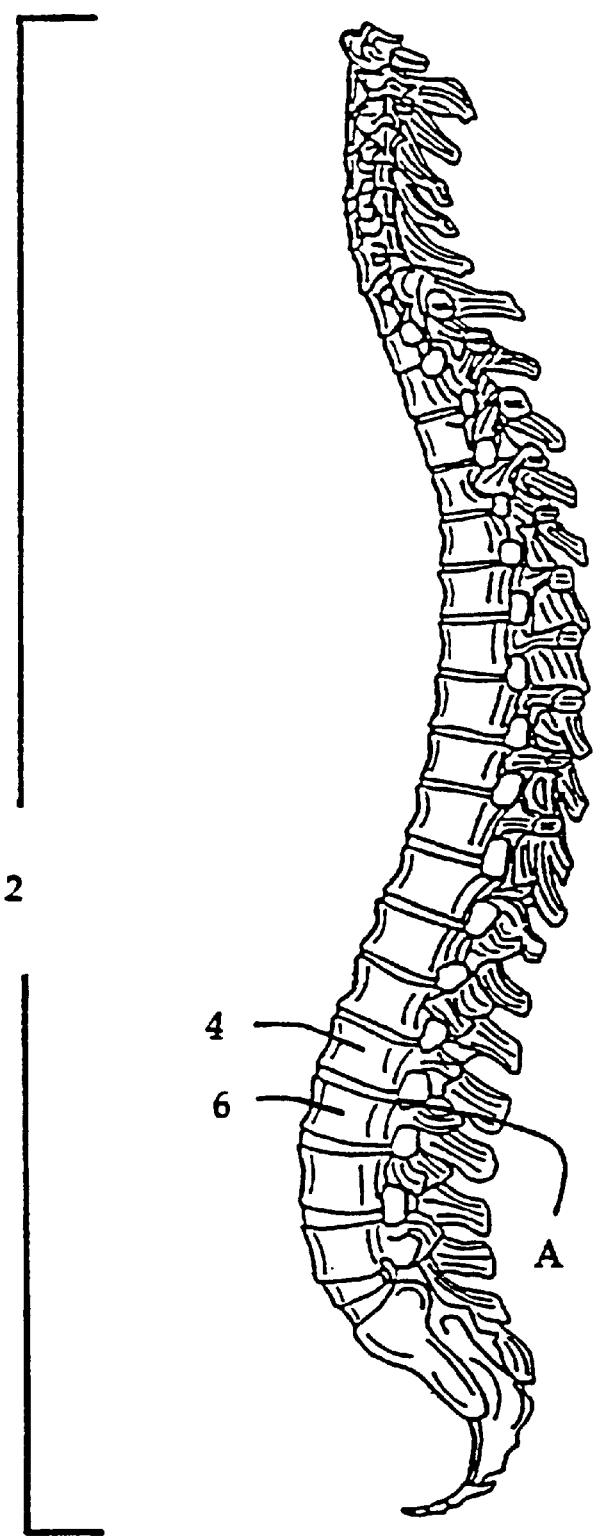
FIG. 1 is an illustration of the spine of a human showing the location of one method of inserting an epidural catheter tube.

"Subject" as used herein refers to a vertebrate. Preferably, the vertebrate is a human.

"Catheter" as used herein refers to a tubular medical device for insertion into canals, vessels, passageway or body cavities to permit injection or withdrawal of fluids or to keep a passage open wherein the fluid travels in the interior of the tubular structure. A preferred catheter is capable of insertion into an epidural space of a subject having a spine for the introduction of fluid. In such a catheter, there may be a metal element disposed within the catheter for the conduction of electricity. The metal element may extend to the end of the catheter such that the metal element is exposed outside of the catheter for conducting electricity directly to the epidural space of the subject. In this instance, the metal element is preferably removable from the catheter such that the metal element is not exposed to the epidural space of the subject for prolonged periods of time. However, in a preferred embodiment, the metal element does not extend to the end of the catheter such that, when it is inserted into an epidural space of a subject there is no directly exposed metal component in the epidural space of the subject In this instance, an aqueous solution capable of conducting electricity is used, as described below, such that the metal element conducts electricity indirectly to the epidural space of the subject as a result of the aqueous solution.

Alternately, the catheter may be comprised of a hollow needle such that fluids may be conducted therethrough to a distal end of the needle. The fluids may be conducted directly through the bore of the needle or through a suitable second catheter, having an outside diameter smaller than the diameter of the bore of the needle, which may be inserted in the bore. In this alternate embodiment, the needle is preferably suitable for insertion into the epidural space of the spine of the subject and preferably has sufficient rigidity to permit epidural placement percutaneously. The distal end of the needle is provided for contacting the epidual space of the spine and directing conducting electricity thereto. Further, the needle preferably includes an insulating coating about at least a portion of the needle for inhibiting the conduction of electricity therethrough. However, the distal end of the needle is exposed outside of the insulating coating for contacting the epidural space.

"Aqueous solution" as used herein refers to a liquid capable of conducting electricity. In one embodiment, the aqueous solution is water based and may be a "saline solution" (e.g., a solution of water with potassium, sodium and/or magnesium salt). In a preferred embodiment, the aqueous solution is isotonic. Another preferred aqueous solution is a solution comprising an anesthetic such as an "epimorphine solution" (e.g., a morphine solution designed for epidural injection, e.g., 1 to 5 mg dosages at 0.5 mg/ml or 2 to 10 mg doses at 1 mg/ml).

"Epidural space" as used herein is the space defined between the ligamentum flavum on the posterior or back side of the spinal cord and the anterior longitudinal ligament on the anterior or frontal side of the spinal cord.

"Motor response" as used herein refers to a reaction of the body of a subject to an electrical stimulus to the epidural space. Commonly, the motor response-is muscle spasm or twitch.

"Connector" as used herein refers to an element designed to attach to the end of a catheter and adapted to connect with a fluid control means (e.g., a syringe) such that fluid may be introduced to or withdrawn from the catheter.

"Conductive element" as used herein refers to an element capable of conducting electricity to the inside of a catheter. In the preferred embodiment, such introduction may be due to direct communication with the inside of the catheter or with a electrically conductive material (solid or liquid) that is in communication with the inside of a catheter. Commonly, the conductive element is metal, and in a preferred embodiment, the conductive element is a screw. However, the conductive element may be comprised of either a hollow or a non-hollow needle.

"Electrical conduction means" as used herein refers to an element capable of introducing electricity to the interior of a catheter that is attached to a source of electricity in a preferred embodiment, the electrical conduction means is a connector having a conductive element that is connected to a source of electricity.

"Unable to communicate" as used herein refers to a subject that is unable to effectively communicate paresthesia or anesthetic effect on the subject's pain or perception of pain to a treating physician. This condition may be the result of the nature of the subject (e.g., speaks a language foreign to the physician or is not human) or may be the result of the subject's condition (e.g., age of the subject or due to a condition preventing communication, such as being mute). Commonly, the subject will be unable to communicate due to being "unconscious" (unable to perceive any extracorpeal stimulus).

"Anesthetic" as used herein refers to a chemical composition, the application of which can reduce a subject's perception of pain.

DETAILED DESCRIPTION OF THE INVENTION

Figure 2:
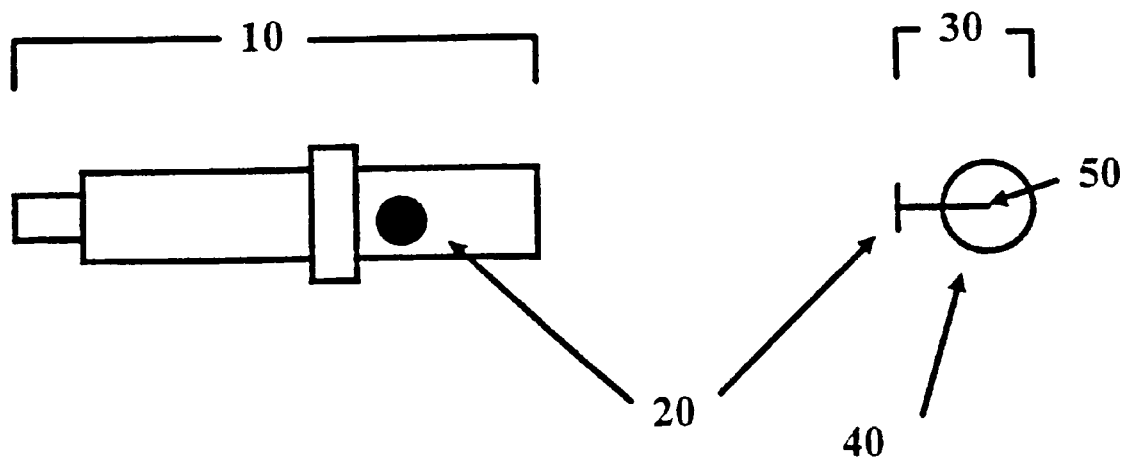
FIG. 2 is an illustration of a modified epidural catheter connector useful in one embodiment of the present invention.
Figure 3:
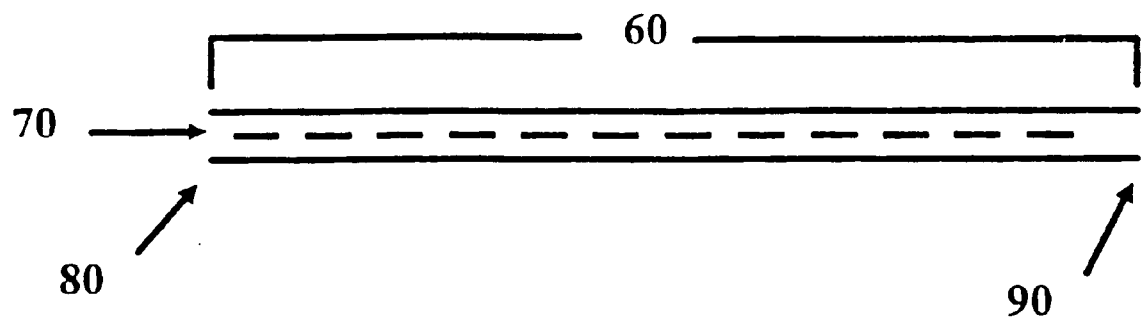
FIG. 3 is an illustration of an epidural catheter with a wire disposed therein, useful in one embodiment of the present invention.

In the present invention, a catheter assembly suitable for introduction into an epidural space is provided. In a preferred embodiment, the catheter assembly comprises a catheter tube of a size suitable for insertion into an epidural space, a connector attached to the proximal end of the catheter tube, and a connector having a conductive element When desired, an appropriate connector may be constructed with modification of existing epidural catheter connectors. For example, the connector by Smiths Industries (sold by Concord/Portex and descbed in U.S. Pat. No. 5,464,400, herein incorporated by reference) can be modified with an electrode. FIG. 2 shows such a modification. The connector shown in side view has an electrode inserted 20. Likewise, the same electrode 20 is shown in the connector in top view 30, demonstrating the that the electrode extends from the outside of the connector 40 to the interior lumen of the connector 50. Thus, in this embodiment an electric source may be attached to the electrode 20 on its outer exposed portion and the electric current will reach the interior lumen 50 of the connector.

For this preferred embodiment, the catheter is placed in an epidural space of a subject and the conductive element is attached to an electric source. An aqueous solution capable of conducting electricity is introduced into the catheter and an electric current is applied to the conductive element of the connector. The electric current provides a stimulus to the region of placement of the catheter and motor responses by the subject indicate the successful placement of the catheter. For example, if the subject exhibits motor responses at low current (ie., 1–10 mA), the catheter has been inserted into the epidural space. On the other hand, if the subject only exhibits a motor response at a higher current (ie., >10 mA), then the catheter is outside of the epidural space. If the subject exhibits a motor response at a very low current (ie., <1 mA), the catheter may be placed in subaracinoid space, subdural space or directly against a spinal root. Of course, these amperage settings are intended as guidelines and can be readily adjusted for the individual subject and/or species.

In addition to determining the proper placement in an epidural space, the present invention can be utilized to avoid an improper vascular placement in the epidural space. For example, by observance of the current required for motor response before and after a test dose of local anesthetic injected (e.g., 3 to 6 ml test dose of 1.5% lidocaine) into the epidural space, one may also detect the intravascular placement of catheter within an epidural space. In proper epidural catheter placement, the minimum current required to exhibit a subject's motor response will gradually increase over time. On the other hand, this minimum current will remain unchanged if the placement of the catheter is intravascular as the injected local anesthetic is inadvertently injected systemically rather than locally. Thus, the present invention is useful in determining proper placement of a catheter into an epidural space as well as determining if the catheter is improperly inserted intravascularly in the epidural space.

It should be understood that the terms "distal" and "proximal" as used herein mean the following. The distal end of the catheter is the tip of the catheter which is first inserted into the epidural space. The proximal end is the opposite end of the catheter.

While the present invention is not limited by the nature of the catheter tube, in one embodiment, it will be of a size suitable for placement in an epidural space. The catheter size is preferably that of a number 4 French body (1.67 mm). The usable length of the catheter is not critical and may be approximately 45–180 cm. The particular material of which the catheter is made is not critical and may be any of the types of material used in known catheters, such as known bipolar cardiac pacing catheters.

While the catheter will normally be sufficiently rigid to permit epidural placement, if the materials used do not permit sufficient rigidity for this purpose, a stylet may be used to control the placement of the catheter. In this case a stylet passage is present which permits insertion of the stylet into the catheter. Likewise, a stylet may be inserted into the catheter via passage for purposes of manipulating the catheter during placement in the epidural region. Other catheters and systems and methods for inserting spinal catheters are set forth in U.S. Pat. Nos. 4,973,312; 4,985,022; 5,069,674; and 5,135,525 all herein incorporated by reference.

The catheter, when in use, is inserted into the spinal epidural space. This may be accomplished by means of a 15, 16 or 17 gauge epidural needle or it may be applied directly during spinal surgery. Special needles for epidural injection are described in U.S. Pat. No. 5,628,734, herein incorporated by reference.

The method of using an epidural injection needle in administering an epidural anesthetic preferably employs the midline approach. The midline approach is known to the ordinary skilled artisan and, therefore, will not be described here in detail. A description of this method can be found in the Illustrated Handbook of Local Anesthesia, Year Book Medical Publishers, Inc., 1969. It should be understood, however, that an injection needle may also be employed in a spinal injection made using the lateral approach Air lock within the catheter or high resistivity aqueous solutions may hinder the flow of current down the length of the catheter tube. Therefore, in one embodiment of the present invention a metal element is disposed within the lumen of the catheter tube to ensure proper conduction of electricity through the length of the catheter. In one embodiment, the metal element is a wire. In such an embodiment, the wire may be connected to the conductive element of the connector and traverse the length of the catheter tube. To avoid electrochemical reaction of the metal element to the subject's dural tissue in the presence of the fluid contents of the catheter tube or the subject's body fluids, in a preferred embodiment, the metal element does not reach the end of the catheter tubing such that no metal element is directly contacting the subject's dural tissue. One embodiment of a wire within a catheter is illustrated in FIG.

3. A catheter tube (60) has a wire (70) extending from the catheter's proximal end (80) toward the distal end (90), but the wire (70) does not extend entirely to the distal end.

As indicated, the metal element is preferably comprised of a wire as described above. However, the metal element may be comprised of any metal device or structure suitable for this purpose, such as a hollow or non-hollow needle.

Further, in the preferred embodiment described above, the metal element does not extend to the distal end of the catheter and an aqueous solution is used for conducting electricity from the metal element to the epidural space of the subject. However, alternately, the metal element may extend to the end of the catheter such that the metal element is exposed outside of the catheter. In this instance, the metal element conducts the electricity directly to the epidural space of the subject.

However, where the metal element conducts electricity directly to the epidural space, the metal element preferably does not contact, and is not exposed to, the epidural space of the subject for extended periods of time. As a result, the metal element is preferably removable in this embodiment. In order to facilitate the removal of the metal element, the metal element is also preferably comprised of a needle in this embodiment. Thus, once the location or placement of the catheter is confirmed by electrical stimulation, the removable needle is removed or withdrawn, at least in part, such that its distal end is no longer exposed outside the distal end of the catheter. Accordingly, the metal of the needle is no longer in direct contact with the epidural space. More preferably, the needle is withdrawn completely from the catheter so that no rigid objects or elements remain in the epidural space of the subject Further, the catheter itself may be comprised of a hollow needle such that fluids may be conducted therethrough to a distal end of the needle. The fluids may be conducted directly through the bore of the needle. Alternately, the fluids may be conducted through a suitable second catheter, having an outside diameter smaller than the diameter of the bore of the needle, which is inserted in the bore. The distal end of the needle defines the distal end of the catheter and is provided for contacting the epidural space of the spine of the subject. Thus, electricity is conducted to the epidural space directly by the distal end of the needle. Further, the needle is suitable for insertion into the epidural space of the spine of the subject and preferably has sufficient rigidity to permit epidural placement percutaneously. As well, the hollow needle of this embodiment preferably includes an insulating coating for inhibiting the conduction of electricity therethrough. The insulating coating may cover all or a portion of the outer surface of the needle. However, in any event, the distal end of the needle is exposed outside of the insulating coating for contacting the epidural space. As a result, the electricity is conducted to the distal end of the catheter.

Preferably, in this alternate embodiment, the hollow needle is not left in the epidural space for extended periods of time. Therefore, once the location or placement of the catheter is confirmed by electrical stimulation, an injection of an anesthetic or other medication may be introduced into the epidural space and the hollow needle is preferably subsequently withdrawn. Further, the second smaller diameter catheter described above may be inserted into the epidural space through the bore of the needle. The second smaller diameter catheter may then be left in the epidural space and used for the administration of medications following the withdrawal or removal of the needle.

Figure 5:
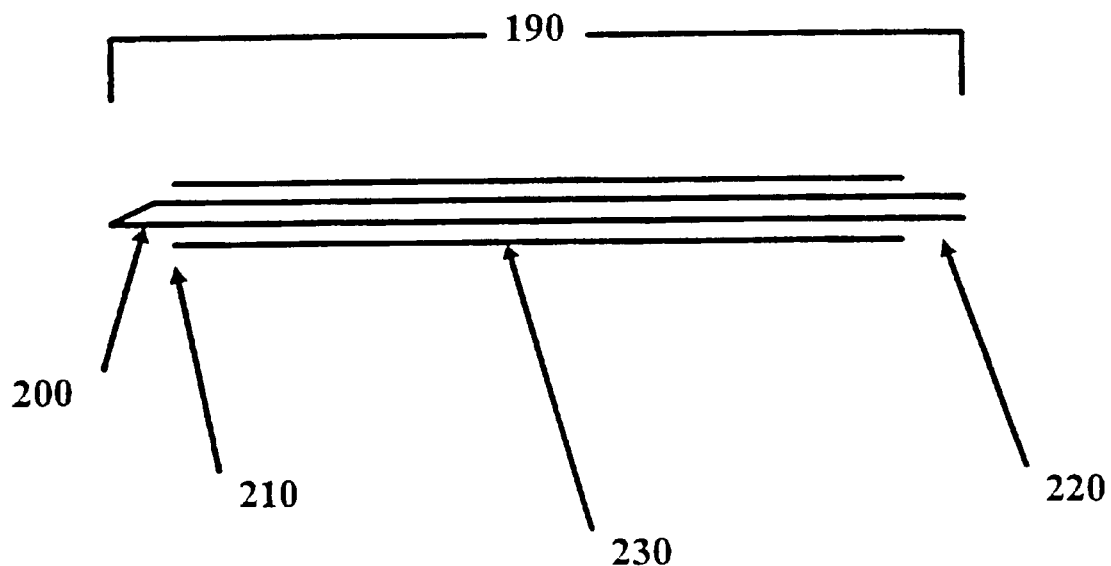
FIG. 5 is an illustration of an epidural catheter comprised of a hollow needle having an insulating coating.

This alternate embodiment of the invention is further illustrated in FIG. 5. Referring to FIG. 5, the catheter (190) is comprised of the hollow needle (200) for conducting fluids, such as an anesthetic, therethrough from a proximal end (220) to the distal end (210) of the needle (200). The distal end (210) of the needle (200) defines the distal end of the catheter for contacting the epidural space of the spine of the subject. Further, the insulating coating (230) extends substantially between the proxamal end (220) and the distal end (210) of the needle (200). Although the insulating coating (230) may be comprised of a separate tubular element formed from an insulating material for receiving the needle (200) therein, the insulating coating (230) is preferably comprised of a layer of an insulative material integral with or affixed to the outer surface of the needle (200). The distal end (210) of the needle (200) is exposed outside the insulating coating (230) such that the distal end (210) may contact the epidural space and conduct electricity thereto. The proximal end (220) of the needle (200) is attached to or is connected or communicates with a source of electricity. Thus, electricity is conducted through the needle (200) inside the insulated coating (230) from the proximal end (220) to the distal end (210) such that the electricity is directly conducted to the epidural space.

The present invention is not limited by the electrical source. In a preferred embodiment, the electrical source comprises a nerve stimulator, such at the Dakmed Model 750 with digital display. Likewise, while the present invention is not limited to a specific method of introducing electricity to a conductive element, in one embodiment the negative lead from a nerve stimulator is connected to the conductive element of the connector and the positive lead is connected directly to the subject Drugs (medicaments) are inserted into the epidural region by the catheter by injection from a drug administering device, such as a hypodermic syringe, and directed to the interior of the catheter. The drug exits the catheter through the outlet opening on the distal end of the catheter. While the present invention is not limited by the nature of the medicant, one medicant suitable is described in U.S. Pat. No. 5,545,648, herein incorporated by reference. Where the catheter comprises a hollow needle as described above, the drugs may be directly inserted into the epidural region by injection through the distal end of the needle.

The catheter of the present invention may be used not only on human subjects but also on other animals, preferably vertebrates, and most preferably mammals. As animals other than humans cannot communicate to express anesthetic effect, an objective means of determining the proper placement the catheter becomes very valuable.

The following example serves to illustrate a certain preferred embodiment and aspects of the present invention and is not to be construed as limiting the scope thereof.

EXAMPLE 1

Figure 4:
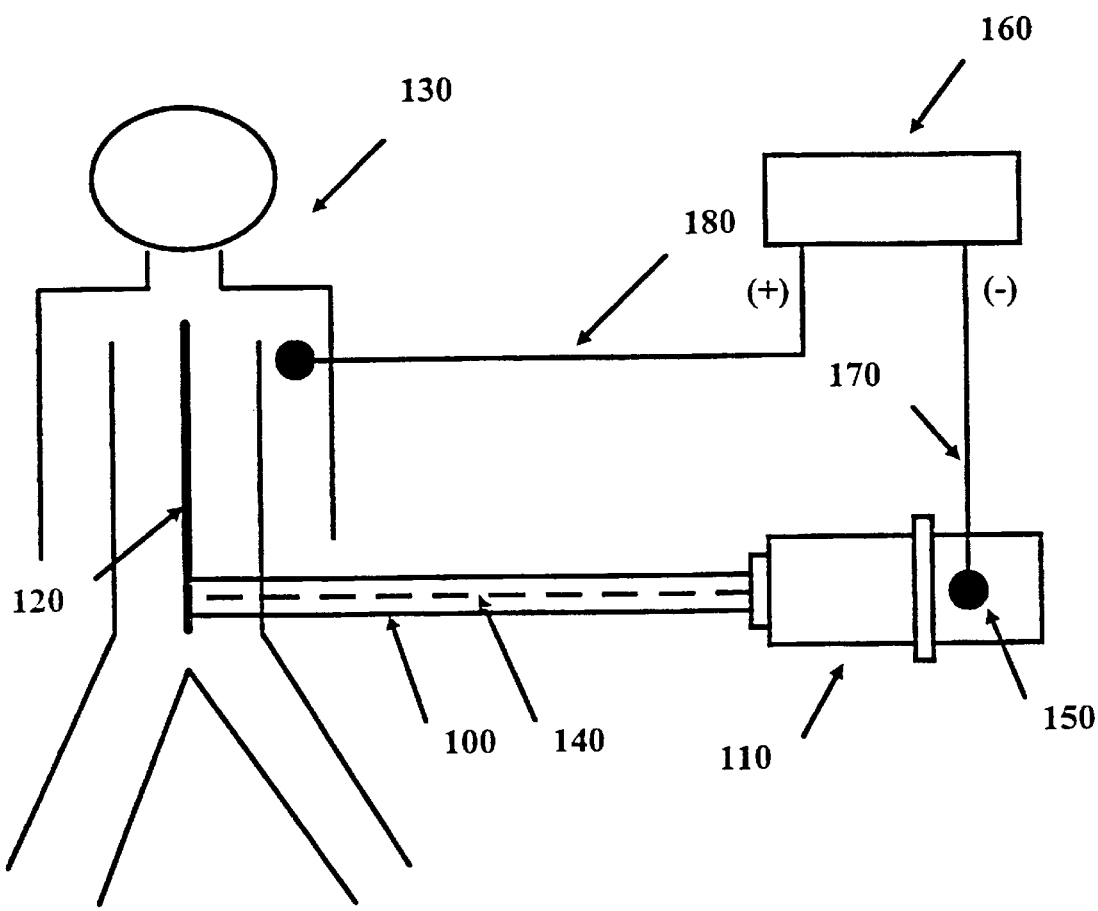
FIG. 4 is a schematic illustration of the clinical use of one embodiment of the present invention.

In this example, a method of using low current stimulus through an epidural catheter to determine proper placement of the catheter is described. FIG. 4 is a schematic diagram of the method described in this example.

A catheter (100) with a connector (110) on its proximal end is inserted into an epidural space (not shown) of the spine (120) of a subject (130). A wire (140) is disposed within the catheter (100) and extends from a conductive element (150) on the corrector (110) down through the catheter (100), but does not reach the distal end (not shown) of the catheter (100).

The conductive element (150) of the connector (110) is set such that it communicates with the inner cavity (not shown)

of the connector (110) near, preferably touching, the wire (140), as well as extending outside the connector (110) such that it can be attached to an electric source (160). The electric source (160) is a nerve stimulator (Dakmed Model 750 digital) set at 1 Hz.

In operation, the distal end of the catheter (100) is placed in the region of an epidural space. Saline solution is introduced into the catheter (100) and the negative lead (170) from the electric source (160) is attached to the conductive element (150). The positive lead (180) from the electric source (160) is attached to the subject (130). Low current electrical stimulation is provided by the electric source (160) and motor response from the subject (130) is assessed. The output current is gradually increased from zero mA at 1 Hz (one pulse per second) until a motor response of the subject (130) is visible. If the subject responds to low amperage current (ie., 1 to 10 mA), the placement of the catheter is correct. If the subject (130) only responds to higher amperage current, the catheter is not in an epidural space.

EXAMPLE 2

Using sterile technique, a nerve stimulator (Dakmed model 750 digital) is connected to an existing epidural catheter via an ECG adaptor (Arrow Corporation as described in U.S. Pat. No. 4,644,960, herein incorporated by reference). 0.2–1 ccs of sterile normal saline solution is injected via the catheter to prime the catheter and the ECG adaptor. The negative lead of the nerve stimulator is attached to the metal hub of the ECG adaptor. The nerve stimulator frequency is set at a rate of 1 Hz. The output current is gradually increased from zero until motor activity/twitch response is visible. Depending on the observed positive or negative response to low current stimulation (1 to 10 mA), the catheter's placement is considered to be correct or incorrect. A standard test dose (3 ml of 1.5% lidocaine with 1:200,000 epinephrine) is then injected.

The subject is then assessed clinically for any change in heart rate, blood pressure and sensory functions in 3 minutes. By observing the minimum current required for motor responses before and after this test dose, intravascular placement can be detected. The minimum current required to induce a motor response increases after the standard test dose is administered if the catheter is placed properly in the epidural space (ie., not intravascularly). If the catheter is improperly placed intravascularly in the epidural space, the minimum current required to induce a motor response is unchanged.

EXAMPLE 3

This example teaches a method of producing a connector dimensioned such that it is suitable for connection to an epidural catheter, such connector having a conductive element suitable for connection to a source of electricity. FIG. 2 illustrates the product. A metal sheet metal screw 20 is inserted into the side of an epidural catheter connector 10 (commercially available from Smith Industries, Keene, N.H.). The metal screw 20 is suitable as a conductive element in the connector 10.

EXAMPLE 4

This example provides an alternative method of producing a connector dimensioned such that it is suitable for connection to an epidural catheter, such connector having a conductive element suitable for connection to a source of electricity. An epidural catheter connector (Flextip Plus™, Arrow International Inc., Reading, Pa.) is connected to an Arrow-Johans ECG Adapter for right atrial electrocardiography (RAECG, Arrow International Inc., Reading, Pa.), having a conductive element.

From the above, it is clear that the present invention provides a simple and effective method for determining the proper placement of a catheter. into an epidural space prior to the introduction of anesthesia.

EXAMPLE 5

Figure 6:
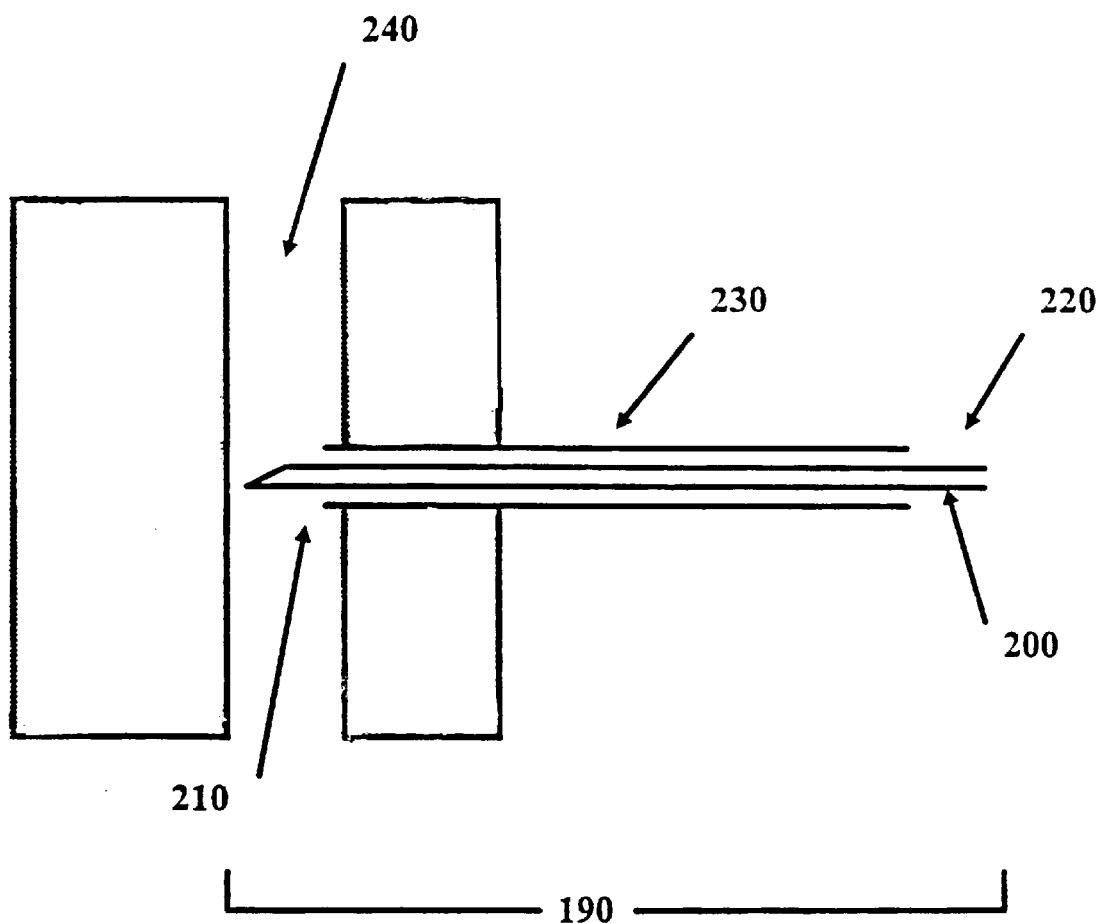
FIG. 6 is a schematic illustration of the clinical use of the epidural catheter shown in FIG. 5.

Referring to FIGS. 5 and 6, in this example, a method and device are provided for confirming the placement of a catheter (190) in the epidural space of the spine of the subject using low current stimulus conducted through a hollow needle (200) directly to the epidural space. In this embodiment, the catheter (190) comprises the hollow needle (200) for conducting fluids therethrough. In particular, the fluids are conducted directly through the bore of the needle (200). However, alternately, the fluids may be conducted through a suitable second catheter (not shown), having an outside diameter smaller than the diameter of the bore of the needle, which is inserted in the bore.

Further, the electricity is conducted to a distal end (210) of the needle (200) for contact with the epidural space (240) of the subject. The needle (200) has sufficient rigidity to permit epidural placement percutaneously. As well, the needle (200) has an insulating coating (230) extending substantially between a proximal end (220) and the distal end (210) of the needle (200). The distal end (210) extends outside of the insulating coating (230) and is suitable for insertion into the epidural space (240). The proximal end (220) may also extend outside the insulating coating (230) and is suitable for connection to or communication with an electrical source.

In operation, the negative lead of a nerve stimulator is attached to the proximal end (220) of the needle (200). The nerve stimulator frequency is set at a rate of 1 Hz. The output current is gradually increased from zero until a motor response (twitch response) is visible. Depending upon the observed positive or negative response to low current stimulation (1 to 10 mA), the placement of the catheter is considered to be correct or incorrect. When incorrect, the placement may be adjusted and the method performed again.

The embodiments of the invention in which an exclusive privilege or property is claimed are defined as follows:

1. A method for confirming the placement of a catheter in an epidural space of a spine of a subject, comprising:
    (A) providing:
        (i) a subject in need of having a catheter inserted in the spine;
        (ii) a catheter having first and second ends;
        (iii) an aqueous solution capable of conducting electricity and suitable for administration in the epidural space of said spine of said subject; and
        (iv) an electrical conduction means;
    (B) contacting the epidural space of said spine of said subject with said first end of said catheter,
    (C) attaching said electrical conduction means to said second end of said catheter;
    (D) administering said aqueous solution through said catheter into said epidural space; and
    (E) conducting electricity with said electrical conduction means under conditions such that said aqueous solution conducts electricity to said epidural space.

2. The method of claim 1, further comprising the step f) measuring the motor response of said subject caused by said conducting of electricity.

3. The method of claim 1, wherein said electrical conduction means comprises a connector configured for attachment to said second end of said catheter and having a conductive element in communication with a source of electricity.

4. The method of claim 1, wherein said subject is unable to communicate.

5. The method of claim 4, wherein said subject is unconscious.

6. The method of claim 1, wherein said aqueous solution comprises a saline solution.

7. The method of claim 1, wherein said aqueous solution comprises an epimorphine solution.

8. A method for confirming the placement of a catheter in an epidural space of a spine of a subject, comprising:
   (A) providing:
      (i) a subject in need of having a catheter inserted in the spine;
      (ii) a non-metal-containing catheter having first and second ends;
      (iii) an aqueous solution capable of conducting electricity and suitable for administration in the epidural space of said spine of said subject; and
      (iv) a connector configured for attachment to said second end of said catheter, said connector having a conductive element in communication with a source of electricity;
   (B) contacting the epidural space of said spine of said subject with said first end of said catheter;
   (C) attaching said connector to said second end of said catheter;
   (D) administering said aqueous solution through said catheter into said epidural space;
   (E) conducting electricity with said conductive element of said connector under conditions such that said aqueous solution conducts electricity to said epidural space; and
   (F) measuring the motor response of said subject caused by said conducting of electricity.

9. The method of claim 8, further comprising the step g) administering anesthetic to said subject.

10. The method of claim 8, wherein said subject is unable to communicate.

11. The method of claim 10, wherein said subject is unconscious.

12. The method of claim 8, wherein said aqueous solution comprises a saline solution.

13. The method of claim 8, wherein said aqueous solution comprises epimorphine solution.

14. A method for confirming the placement of a catheter in an epidural space of a spine of a subject, comprising:
   (A) providing:
      (i) a subject in need of having a catheter inserted in the spine;
      (ii) a catheter having first and second ends, said catheter comprising a metal element disposed the length of said catheter and housed completely within said catheter such that no metal is exposed outside said first end of said catheter;
      (iii) an aqueous solution capable of conducting electricity and suitable for administration in the epidural space of said spine of said subject; and
      (iv) a connector configured for attachment to said second end of said catheter, said connector having a conductive element in communication with a source of electricity;
   (B) contacting the epidural space of said spine of said subject with said first end of said catheter;
   (C) attaching said connector to said second end of said catheter;
   (D) administering said aqueous solution through said catheter into said epidural space;
   (E) conducting electricity with said conductive element of said connector under conditions such that said aqueous solution conducts electricity to said epidural space; and
   (F) measuring the motor response of said subject caused by said conducting of electricity.

15. The method of claim 14, further comprising the step g) administering an anesthetic to said subject.

16. The method of claim 14, wherein said metal comprises a wire disposed within said catheter.

17. The method of claim 16, wherein said wire contacts said connector.

18. The method of claim 14, wherein said subject is unable to communicate.

19. The method of claim 18, wherein said subject is unconscious.

20. The method of claim 14, wherein said aqueous solution comprises a saline solution.

21. The method of claim 14, wherein said aqueous solution comprises epimorphine solution.

22. The method as claimed in claim 14 wherein the metal element is comprised of a removable hollow needle such that fluids may be conducted therethrough to a distal end of the needle, wherein the distal end of the needle defines the distal end of the catheter for contacting the epidural space of the spine of the subject and wherein the conducting step is comprised of conducting electricity to the distal end of the catheter via aqueous solution.

23. A method for confirming the placement of a catheter in an epidural space of a spine of a subject, the catheter having a proximal end and a distal end, the method comprising the steps of:
   (A) inserting the distal end of the catheter into the spine of the subject for contact with the epidural space;
   (B) injecting into the epidural space an aqueous solution capable of conducting electricity and suitable for administration in the epidural space;
   (C) conducting electricity to the distal end of the catheter under conditions such that the aqueous solution conducts the electricity to the epidural space; and
   (D) observing an involuntary motor response of the subject caused by conducting the electricity to the distal end of the catheter in order to confirm the placement of the catheter in the epidural space.

24. The method as claimed in claim 23 further comprising the step of administering an anesthetic to the subject.

25. The method as claimed in claim 23 wherein electricity is conducted to the distal end of the catheter at least in part by electrical conduction means.

26. The method as claimed in claim 25 wherein the electrical conduction means is comprised of a conductive element in communication with a source of electricity.

27. The method as claimed in claim 26 wherein the conductive element is comprised of a metal element disposed within the catheter.

28. The method as claimed in claim 23 further comprising the step of adjusting the position of the catheter such that the distal end of the catheter contacts the epidural space of the spine of the subject.

29. The method as claimed in claim 14 wherein the catheter is comprised of a hollow needle such that fluids may be conducted therethrough to a distal end of the needle, wherein the distal end of the needle defines the distal end of the catheter for contacting the epidural space of the spine of the subject and wherein the conducting step is comprised of conducting electricity to the distal end of the needle via aqueous solution.

30. The method as claimed in claim 29 wherein the needle includes an insulating coating about at least a portion of the needle.

31. The method as claimed in claim 30 wherein the subject is unable to communicate.

32. The method as claimed in claim 31 wherein the subject is unconscious.

* * * * *